(12) United States Patent
Ramakrishna et al.

(10) Patent No.: US 9,278,296 B2
(45) Date of Patent: Mar. 8, 2016

(54) METHOD FOR SECURING A DISTRIBUTOR PLATE TO A BACKING PLATE OF A CHROMATOGRAPHY COLUMN AND A CHROMATOGRAPHY COLUMN

(75) Inventors: Manoj Kumar Ramakrishna, Bangalore (IN); Shashikanth Agnihotry, Bangalore (IN)

(73) Assignee: GE Healthcare Bio-Sciences AB, Uppsala (SE)

( * ) Notice: Subject to any disclaimer, the term of this patent is extended or adjusted under 35 U.S.C. 154(b) by 295 days.

(21) Appl. No.: 13/990,160

(22) PCT Filed: Nov. 28, 2011

(86) PCT No.: PCT/SE2011/514333
§ 371 (c)(1),
(2), (4) Date: May 29, 2013

(87) PCT Pub. No.: WO2012/074464
PCT Pub. Date: Jun. 7, 2012

(65) Prior Publication Data
US 2013/0240426 A1 Sep. 19, 2013

(30) Foreign Application Priority Data
Nov. 29, 2010 (GB) .................................. 1020146.5

(51) Int. Cl.
*B01D 15/22* (2006.01)
*G01N 30/60* (2006.01)

(52) U.S. Cl.
CPC ............ *B01D 15/22* (2013.01); *G01N 30/6017* (2013.01); *G01N 30/6021* (2013.01); *G01N 30/6026* (2013.01); *G01N 30/6004* (2013.01); *G01N 30/6047* (2013.01); *G01N 30/6052* (2013.01); *Y10T 29/49826* (2015.01); *Y10T 29/49883* (2015.01)

(58) Field of Classification Search
CPC .............. G01N 30/6004; G01N 30/60; G01N 30/6017; G01N 30/6021; G01N 30/6026; G01N 30/6047; G01N 30/6052
See application file for complete search history.

(56) References Cited

U.S. PATENT DOCUMENTS 5,141,635 A * 8/1992 LePlang et al. ............ 210/198.2
5,753,795 A * 5/1998 Kuypers ....................... 73/23.37
6,139,732 A 10/2000 Pelletier (Continued)

FOREIGN PATENT DOCUMENTS

| CN | 101219287 | 7/2008 |
| GB | 2325868 | 12/1998 |
| WO | WO 96-26436 | 8/1996 |
| WO | WO 96/26436 | 8/1996 |
| WO | 2008/009412 | 1/2008 |
| WO | WO 2009/041877 | 4/2009 |

(Continued)

OTHER PUBLICATIONS

Search Report Dated Mar. 24, 2014 Issued on Corresponding Chinese Patent Application No. 201180057123.3.

*Primary Examiner* — Katherine Zalasky
*Assistant Examiner* — Benjamin Lebron
(74) *Attorney, Agent, or Firm* — Parks Wood LLC

(57) ABSTRACT

The present invention relates to methods for securing a distributor plate to a backing plate of a chromatography column without the need for releasable fixing means as screws or bolts. The invention also relates to chromatographic columns utilizing such methods. The method employs a negative pressure or vacuum that is generated internally within the column to affix the distributor to the backing plate.

14 Claims, 6 Drawing Sheets

(56) References Cited

U.S. PATENT DOCUMENTS

| | | |
|---|---|---|
| 6,352,266 B1 * | 3/2002 | Rigoli .......................... 277/628 |
| 7,553,455 B1 * | 6/2009 | Renzi et al. ................... 422/546 |
| 7,780,853 B2 | 8/2010 | Davis et al. |
| 2004/0182789 A1 | 9/2004 | Gill et al. |
| 2008/0308498 A1 * | 12/2008 | Davis et al. ................... 210/656 |
| 2010/0230340 A1 * | 9/2010 | Bielawski et al. ......... 210/198.2 |

FOREIGN PATENT DOCUMENTS

| | | |
|---|---|---|
| WO | WO 2009-041877 | 4/2009 |
| WO | WO 2009/093952 | 7/2009 |
| WO | WO 2009-093952 | 7/2009 |
| WO | WO 2010-132011 | 11/2010 |
| WO | WO 2012074455 A1 * | 6/2012 |

* cited by examiner

METHOD FOR SECURING A DISTRIBUTOR PLATE TO A BACKING PLATE OF A CHROMATOGRAPHY COLUMN AND A CHROMATOGRAPHY COLUMN

CROSS-REFERENCE TO RELATED APPLICATIONS

This application is a filing under 35 U.S.C. 371 of international application number PCT/SE2011/051433, filed Nov. 28, 2011, published on Jun. 7, 2012 as WO 2012/074464, which claims priority to patent application number 1020146.5 filed in Great Britain on Nov. 29, 2010.

TECHNICAL FIELD

The present invention relates to chromatography columns and their component parts. In particular, the present invention relates to methods for securing a distributor plate to a backing plate of a chromatography column without the needs for bolts or screws.

BACKGROUND TO THE INVENTION

Chromatography columns may be used in industrial processes to purify process liquids and separate substances of interest from process liquids; typical examples include large-scale preparative purification of fine chemicals and pharmaceuticals, together with biological products. Industrial-scale chromatography columns typically comprise a hollow, axially vertical tubular housing or tube including a liquid inlet at the upper end or lower end and through which the buffer and substances to be separated are dispensed to the media bed located within the cavity of the tube, and a liquid collecting system at the other end for collecting substances and buffer. The particulate chromatographic media or bed through which the buffer fluid and/or substances to be separated and purified percolates is located between the liquid inlet and collecting system. An adapter assembly is typically affixed to the upper end of the tubular housing and a base assembly to the lower end where it is bolted to the bottom flanges. Each of these assemblies typically comprises a strong backing plate and a distributor which further supports a bed support: a bed support is a layer of mesh, filter, sinter, screen or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a nozzle, the adapter may be forced toward the bottom of the tube to compress or pressurize the media bed. Generally the base assembly is a fixed structure which is bolted against the bottom flange of the column tube but, in some instances, may also be in the form of a movably slidable piston or adapter.

The backing plate of the base assembly generally acts as a support for the column, being itself supported on legs or some other stand arrangement which allows clearance for outlet pipe work projecting beneath the base assembly. However, in some columns clearance may not be sufficient for easy maintenance.

Prior art adapter and base assemblies are formed by screwing or bolting the distributor plate into the backing plate by means of bolts or screws. As the distributor is made of inert nonmetallic materials, such as plastic, it may become distorted during the operation of the column when it is subjected to internal pressures ranging from −1 bar to +5 bar. To overcome this problem, the distributor is secured to the backing plate with many screws or bolts. This process typically requires helicoil threads being cut into the distributor plate, a process that can be costly and difficult to implement in high quality materials like stainless steel, polypropylene and other materials which are suitable for use in a GMP environment, and securing the distributor to the backing plate using appropriately threaded screws or bolts.

A significant number of such bolts or screws are required (e.g. in 1 meter diameter column there would typically 20 to 40 screws or bolts and for a 2 meter diameter column approximately 100 to 150 screws or bolts) to secure the distributor to the backing plate as the resulting assembly must be able to withstand back compression pressures when, for instance, the column is being packed. The process of securing the distributor plate to the backing plate by the use of screws and/or bolts can be time consuming when the chromatography column is initially being set up for operation. Errors may occur in the set up process when screws or bolts of the wrong length or incorrect bore are used, resulting in a weaker seal between the component parts.

Corrosion of the screws or bolts, and of the screw threads, can occur with time and repeated use of the column. Furthermore, the cleaning and/or maintenance of the column often necessitates the separation of the distributor plate from the backing plate. Once again, this process requires time to carefully unscrew or unbolt the distributor from the backing plate.

There is therefore a need for chromatography columns which have a simpler, cost-effective means of securing the distributor plate to the backing plate to overcome the above mentioned problems encountered in the prior art.

SUMMARY OF THE INVENTION

According to a first aspect of the present invention, there is provided a method of securing a distributor plate to a backing plate of a chromatography column by generating an internal vacuum therebetween. The term 'internal vacuum' as used herein means a vacuum or negative pressure which is produced in the course of operating the chromatography column, in contrast to a vacuum or negative pressure which is exerted by means of applying a negative pressure using a device such as a pump. Thus, for example, the movement of the component parts within a chromatography column can be configured to generate an internal vacuum. In one embodiment, the relative movement of the adapter assembly and the base assembly can be utilized to produce the internal vacuum.

In one aspect, the chromatography column comprises an adapter assembly and/or a base assembly and movement of said adapter assembly and/or said base assembly generates said internal vacuum between said distributor plate and said backing plate.

In another aspect, the method comprises the steps of:
a) providing a chromatography column comprising:
   a tube in contact with an adapter assembly and a base assembly to define a cavity therebetween;
   said cavity being in fluid connection with the exterior of the column via a closable adapter port and/or a closable base port;
   the adapter assembly and/or the base assembly being movable within said cavity;
   at least one of said adapter assembly and said base assembly comprising a backing plate in contact with a distributor plate to define an air pocket therebetween;

said air pocket being in fluid connection with the cavity via a closable passage in the distributor plate of the adapter assembly and/or the base assembly;

b) closing said passage in the adapter assembly and/or the base assembly;

c) moving the adapter assembly and/or the base assembly towards each other to remove air from the cavity;

d) closing the port in the adapter assembly and/or the base assembly;

e) opening the passage in the adapter assembly and/or the base assembly;

f) moving the adapter assembly and/or the base assembly away from each other to remove air from the air pocket; and g) closing the passage in the adapter assembly and/or the base assembly to secure the distributor plate to the backing plate.

In one aspect, the distributor plate is the adapter distributor plate and the backing plate is the adapter backing plate. Alternatively, the distributor plate may be the base distributor plate and the backing plate is the base distributor plate. It will be understood that the method of the invention may involve a column in which both the adapter assembly and the base assembly comprise a backing plate in contact with a distributor plate to define an air pocket therebetween.

In another aspect, the face of the distributor plate in contact with the backing plate is reinforced, for example by ribbing, rods or other suitable forms of reinforcement. The purpose of the reinforcement is to prevent any distortion of the distributor plate when it is subjected to a vacuum or negative pressure.

In one aspect, locating means are used to co-locate the backing plate and the distributor plate.

In a further aspect, the method additionally comprises the step of allowing air to return to the air pocket to release the distributor plate from the backing plate.

In yet another aspect, the method additionally comprises the step of securing the column tube to the base distributor plate by generating an internal vacuum therebetween.

According to a second aspect of the present invention, there is provided a chromatography column comprising a movable adapter assembly and/or base assembly configured to generate an internal vacuum for securing a backing plate to a distributor plate.

In one aspect, the chromatography column comprises:

a tube in contact with an adapter assembly and a base assembly to define a cavity therebetween;

said cavity being in fluid connection with the exterior of the column via a closable adapter port and/or a closable base port;

the adapter assembly and/or the base assembly being movable within said cavity;

at least one of said adapter assembly and said base assembly comprising a backing plate in contact with a distributor plate to define an air pocket therebetween; and each said air pocket being in fluid connection with the cavity via a closable passage in the distributor plate of the adapter assembly and/or the base assembly.

In one aspect, the distributor plate is the adapter distributor plate and the backing plate is the adapter backing plate. Alternatively, the distributor plate may be the base distributor plate and the backing plate is the base distributor plate. It will be understood that both the adapter assembly and the base assembly may comprise a backing plate in contact with a distributor plate to define an air pocket therebetween.

In another aspect, the port or the passage is controlled by manual, electrical or pneumatic means.

In a further aspect, the face of the distributor plate in contact with the backing plate is reinforced, for example by ribbing, rods or other suitable forms of reinforcement. The purpose of the reinforcement is to prevent any distortion of the distributor plate when it is subjected to a vacuum or negative pressure.

In one aspect, the column comprises locating means to co-locate the backing plate and the distributor.

In another aspect, the column is additionally configured to generate an internal vacuum for securing the base distributor plate to the column tube.

BRIEF DESCRIPTION OF THE DRAWINGS

The features and advantages of the invention will become apparent from the following description taken in connection with the accompanying drawings in which:

FIGS. 3 a-e are schematic sectional view of a column according to the invention depicting the various stages of its operation in securing the base distributor plate to the base backing plate by generating an internal vacuum.

FIGS. 4 a and b are schematic sectional front views of a column according to the invention depicting the various stages of its operation in securing the base distributor plate to the base backing plate and the column tube by generating an internal vacuum.

DETAILED DESCRIPTION OF THE INVENTION

Figure 1:
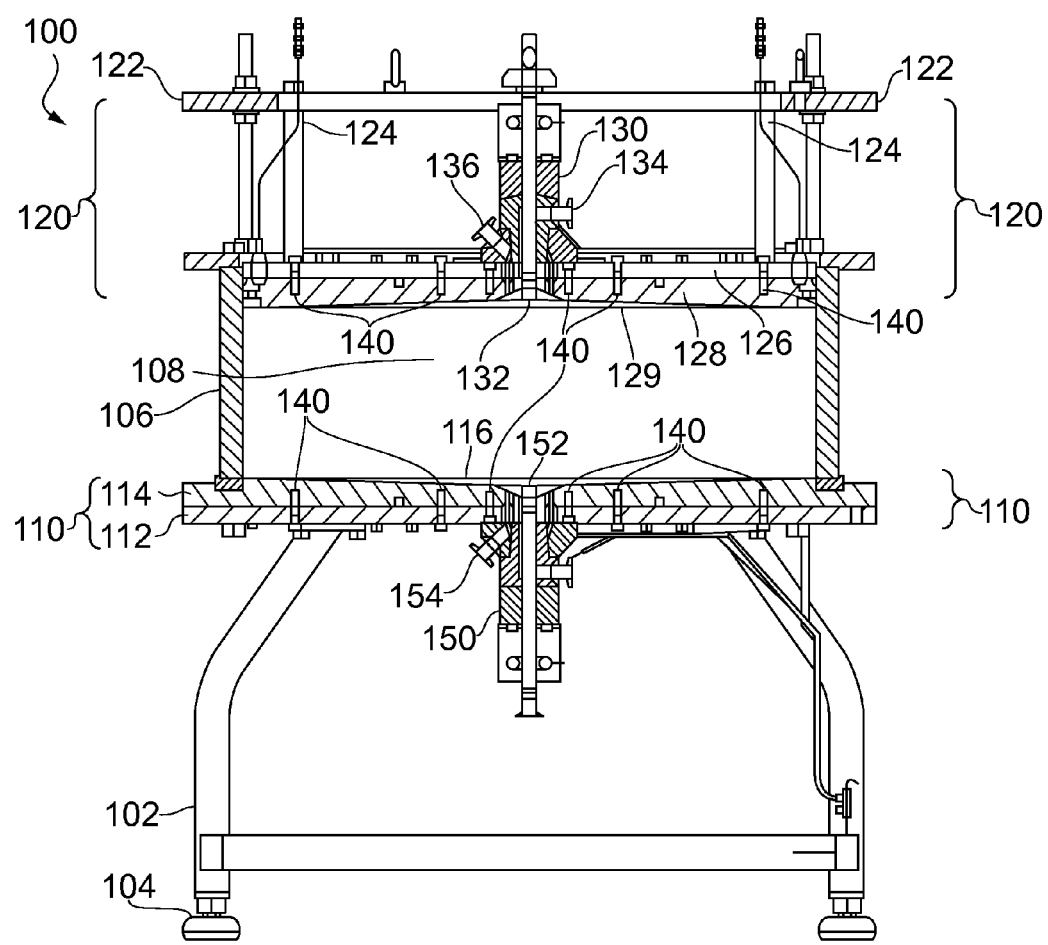
FIG. 1 shows a sectional front view of a chromatography column known in the art in which a distributor plate is secured to a backing plate by screws.

FIG. 1 is a sectional front view of a chromatography column 100 known in the art. The column 100 is made of strong, inert materials such as stainless steel and other materials which are suitable for use in a Good Manufacturing Practice (GMP) environment typical of the pharmaceutical industry. The column 100 is supported on legs 102 having feet 104 which are adjustable in order to modify the height and/or the level of the column. The legs 102 support the column 100 which comprises a cylindrical housing or tube 106 defining a cavity 108, for receipt of chromatographic media, separating a base assembly 110 at one end from an adapter assembly 120 at the other. The tube 106 may typically be made from stainless steel, or other strong, inert materials. Adjacent to the adapter assembly 120 is a dispersion system 130 comprising a nozzle 132 which includes a mobile phase pathway 134, for the introduction of buffer or other suitable mobile phase liquids or chemicals/materials to be separated, and a liquid inlet 136. The adapter assembly 120 may be moveable within the cavity 108 of the tube 106 in an operational mode, for example, to pack or compress a bed of chromatographic media (not shown) present in the cavity 108 which is used to effect chromatographic separation of chemicals within the column. In the figure, the adapter assembly 120 comprises an adapter flange 122, one or more distance pillars 124, a backing plate 126 made typically of stainless steel, a distributor 128 made from inert, non-metallic material which may take the form of a plate having many channels to effect the even distribution of liquids, and a bed support 129 comprising a screen or mesh or filter and optionally a sealing ring (not shown). The bed support 129 may be made of an inert plastic or metal material such as stainless steel. The distributor 128 and bed support 129 are fastened to each other by releasable fixing means (not shown). Typical releasable fixing means 140 which secure the distributor 128 to the backing plate 126 include, but are not limited to, screws and bolts. Generally, the fixing means is a screw which is inserted through a threaded hole in the backing plate 126 into the distributor 128.

The fixing means 140 may be accessed and thus released from the exterior face of the distributor 128 or backing plate 126, that is the face of the plate furthest away from the cavity 108. Access may be gained from the exterior face of the backing plate or distributor to avoid unnecessary exposure of the operator to a suspended or supported load within the column.

The base assembly 110 comprises a backing plate 112 and a distributor 114, fastened to each other by releasable fixing means 140, and a bed support 116. The backing plate 112 is made typically of stainless steel while the distributor 114 may take the form of a plate having many channels to effect the even distribution of liquids. The bed support 116 comprises a screen or mesh or filter and optionally a sealing ring (not shown) and is attached to the distributor 114 by releasable fixing means (not shown). The bed support 116 may be made of an inert plastic or metal material such as stainless steel. The fixing means 140 can take the form of a screw or bolt inserted through corresponding holes around the perimeter of the components; typically the fixing means is a screw which is inserted through a hole in the backing plate 112 into a threaded aperture in the distributor 114. In the example shown, access is obtained from the exterior face of the backing plate 112 to avoid operator exposure beneath a suspended load.

It will be understood that separation of chemical or biological materials on the column, when the cavity 108 is full of chromatographic media, can be carried out in either a downward or upward flow. Thus, in a downward flow, liquid containing chemical or biological materials to be separated is introduced through nozzle 132 and moves in a downward direction through the bed of media, to be collected in the collection system at the base of the column through nozzle 152 of dispersion system 150 via an outlet port 154. In upward flow mode, liquid containing materials to be separated is introduced via the bottom nozzle 152 and flows upwards through the media bed to be collected at the top of the column via nozzle 132 and inlet 136.

Figure 2:
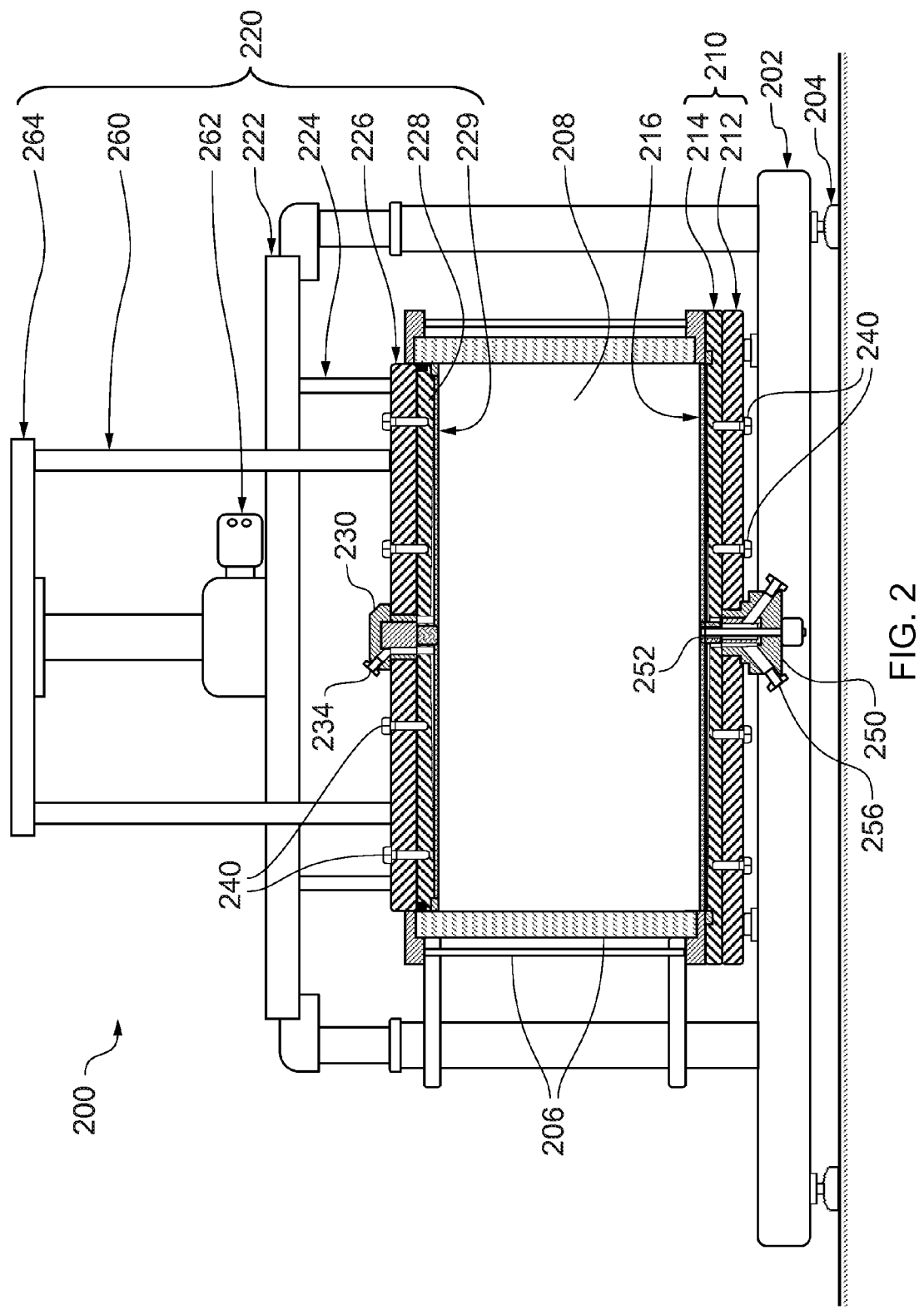
FIG. 2 is a schematic sectional front view of a different prior art chromatography column known in the art in which the distributor plate in which fixing means are used to secure a distributor plate to a backing plate.

FIG. 2 is a sectional front view of a chromatography column 200 known in the art. The column 200 is made of strong, inert materials such as stainless steel and other materials which are suitable for use in a GMP environment typical of the pharmaceutical industry. The column 200 is supported on stand 202 having feet 204 which are adjustable in order to modify the height and/or the level of the column. The stand 202 supports the column 200 which comprises a cylindrical housing or tube 206 defining a cavity 208, for receipt of chromatographic media, separating a base assembly 210 at one end from an adapter assembly 220 at the other. The tube 206 may typically be made from stainless steel, or other strong, inert materials. Adjacent to the base assembly 210 is a dispersion system 250 comprising a nozzle 252 which includes a mobile phase pathway 256, for the introduction of buffer or other suitable mobile phase liquids or chemicals/materials to be separated, and a liquid inlet 254. The adapter assembly 220 may be moveable within a cavity 208 of the tube 206 in an operational mode, for example, to aspirate media, to prime the column, or to pack or compress the bed of chromatographic media used to effect chromatographic separation of chemicals within the column.

In FIG. 2, the adapter assembly 220 comprises an adapter flange 222, one or more distance pillars 224, one or more connecting rod 260, top plate 264, a backing plate 226 made typically of stainless steel, drive system 262, a distributor 228 made from inert, non-metallic material which may take the form of a plate having many channels to effect the even distribution of liquids, and a bed support 229 comprising a screen or mesh or filter and optionally a sealing ring (not shown). The bed support 229 may be made of an inert plastic or metal material such as stainless steel. The distributor 228 and bed support 229 are fastened to each other by releasable fixing means (not shown). Typical releasable fixing means 240 which secure the distributor 228 to the backing plate 226 include, but are not limited to, screws and bolts. Generally, the fixing means is a screw which is inserted through a threaded hole in the backing plate 226 into the distributor 228. The fixing means 240 may be accessed and thus released from the exterior face of the distributor 228 or backing plate 226 that is the face of the plate furthest away from the cavity 208. Access may be gained from the exterior face of the backing plate or distributor.

The base assembly 210 comprises a backing plate 212 and a distributor 214, fastened to each other by releasable fixing means 240, and a bed support 216. The backing plate 212 is made typically of stainless steel while the distributor 214 may take the form of a plate having many channels to effect the even distribution of liquids. The bed support 216 comprises a screen or mesh or filter and optionally a sealing ring (not shown) and is attached to the distributor 214 by releasable fixing means (not shown). The bed support 216 may be made of an inert plastic or metal material such as stainless steel. The fixing means 240 can take the form of a screw or bolt inserted through corresponding holes around the perimeter of the components; typically the fixing means is a screw which is inserted through a hole in the backing plate 212 into a threaded aperture in the distributor 214.

It will be understood that separation of chemical or biological materials on the column, when the cavity 208 is full of chromatographic media, can be carried out in either a downward or upward flow. Thus, in an upward flow, liquid containing chemical or biological materials to be separated is introduced through dispersion system 250 via inlet 256 and nozzle 252 and moves in an upward direction through the bed of media, to be collected in the collection system from the top of the column through dispersion system 230 via an outlet port 234. In downward flow mode, liquid containing materials to be separated is introduced through dispersion system 230 via an outlet port 234 and flows downwards through the media bed to be collected at the bottom of the column through dispersion system 250 via nozzle 252 and port 254.

FIGS. 3 a-e is a schematic sectional view of a column according to the invention depicting the various stages of its operation. The figure details the method of securing the distributor plate 314 to a backing plate 312 of the base assembly 310 by the generation of an internal vacuum between the components but it will be understood that the same principle would be applicable for securing the distributor plate 328 to the backing plate 326 of the adapter assembly 320. It will also be understood that columns according to the invention may consist of a combination of adapter and base assemblies where one or both assemblies secure the distributor plate to the backing plate by means of an internally generated vacuum.

Figure 3A:
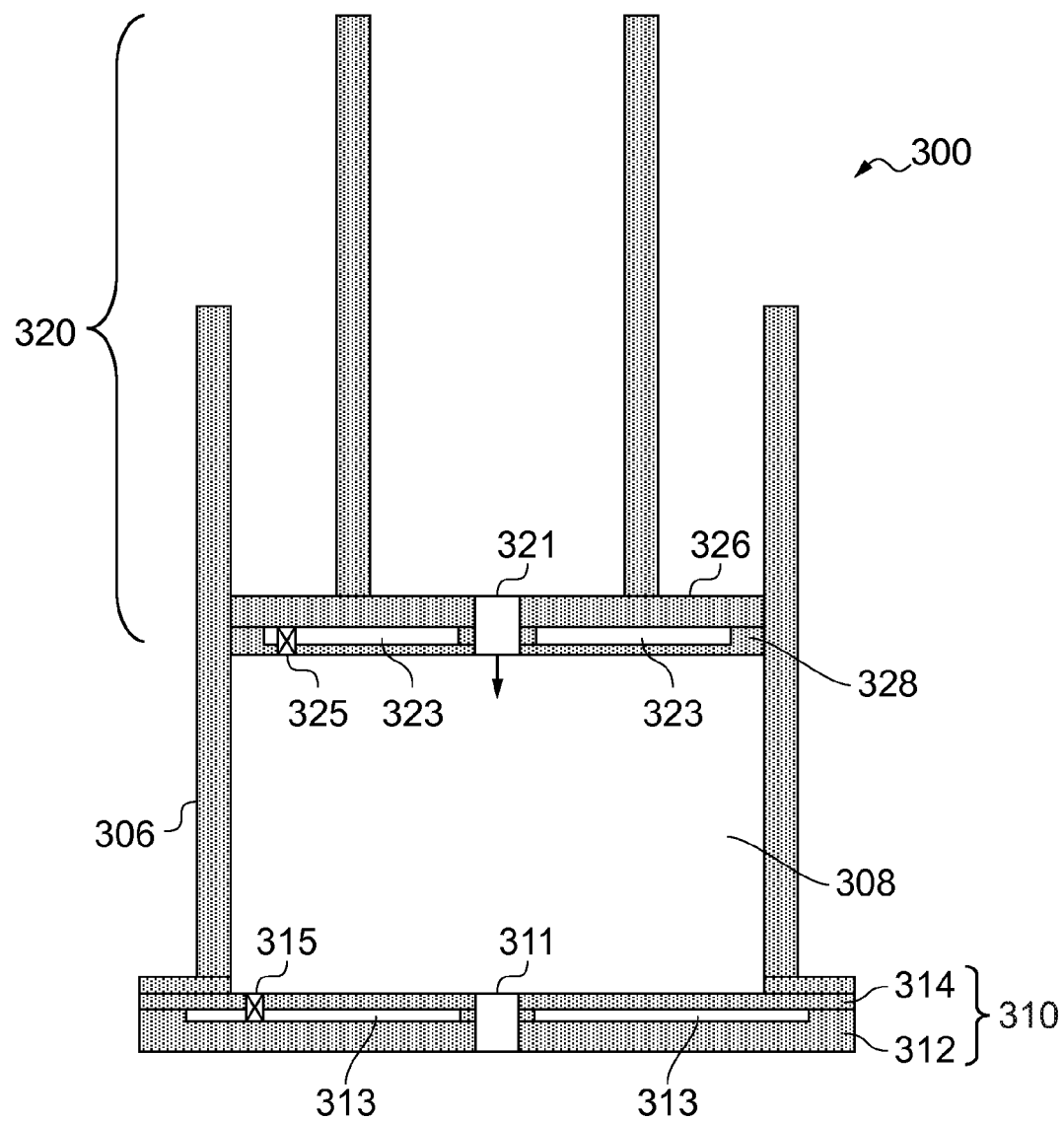
FIG. 3a is a sectional front elevation of a column according to the invention with ports 311 and 321 open prior to expelling air from cavity 308.

The column 300 of FIG. 3a comprises a base assembly 310 and an adapter assembly 320 in contact with a tube 306 to define a cavity 308, which is filled with air, for containment of chromatographic media (not shown). The base assembly 310 comprises a backing plate 312 which is in contact with a distributor plate 314; the contacting surfaces of the plates 312 and 314 are configured such that a cavity or air pocket 313 is formed when they are in contact. The distributor plate 314 may reinforced, as for example by ribbing 314', to prevent distortion when it is stressed. Furthermore, the base assembly 310 has a closable port 311 which is in fluid connection with the cavity 308 and the exterior of the column. With ports 311 and 321 open, passages 315 and 325 are closed and air is removed from the cavity 308 by moving the adapter assembly 320 and the base assembly 310 towards each other, typically by moving the adapter assembly 320 towards the base assembly 310.

Following removal of air from the cavity 308, ports 311 and 321 are closed and one or both of the base assembly passage 315 and the adapter assembly passage 325 are opened. In the example given in FIG. 3b, both passages 315 and 325 are in the open configuration.

Figures 3B, 3C:
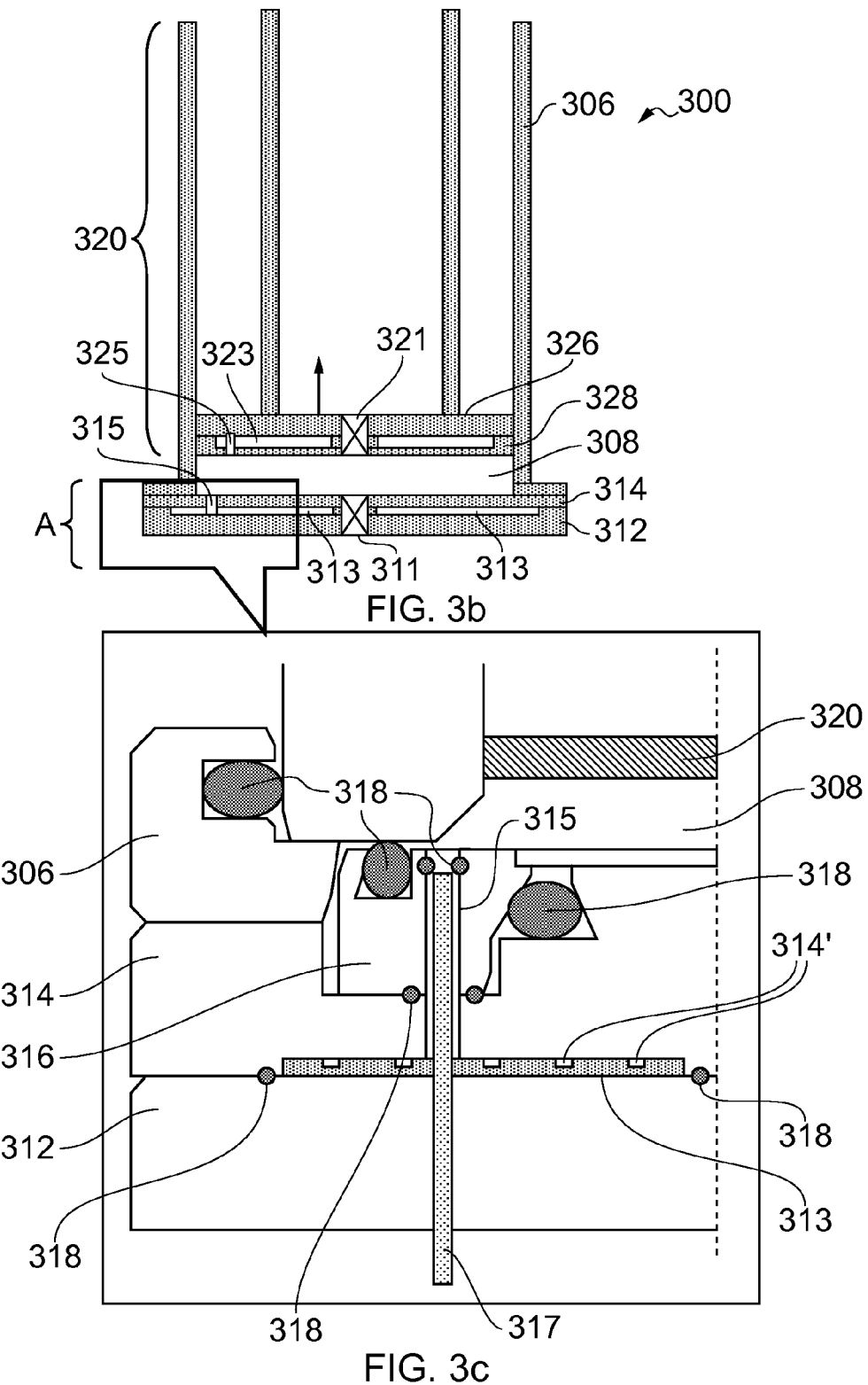
FIG. 3b is a sectional front elevation of the column of FIG. 3a having expelled air from cavity 308.
FIG. 3c is an inset of portion A of the column of FIG. 3b.

FIG. 3c is an enlarged inset giving the detail of section A of the column 300. While the inset shows how an actuator 317 controls the opening and closing of the passage 315 it will be understood that other means are available for controlling this process and that other embodiments of the invention are feasible (e.g. electrical/manual/pneumatic actuated or any other valves controlling the opening and closing of passage). The actuator 317 is free to move within the base backing plate 312, air pocket 313 and passage 315, shown here as a bore hole within the base distributor plate 314 and the base bed support 316. A series of gaskets or o-rings 318 of different sizes provide air-tight seals between the component parts (e.g. between the baking plate 312 and the distributor plate 314, between the bed support 316 and the distributor 314). In the figure, the actuator 317 is in the open position such that there is a fluid connection between the air pocket 313 and the cavity 308. The actuator 317 will be in this open or resting position when there is no vacuum within the cavity 313. The adapter 320 and base 310 assemblies are then drawn apart, typically by raising the adapter assembly 320 within the tube 306, to draw air from the air pocket 313 via open passage 315. As there is no differential pressure on either side of the distributor plate 314 the plate 314 will not become twisted or deformed in any way.

Figures 3D, 3E:
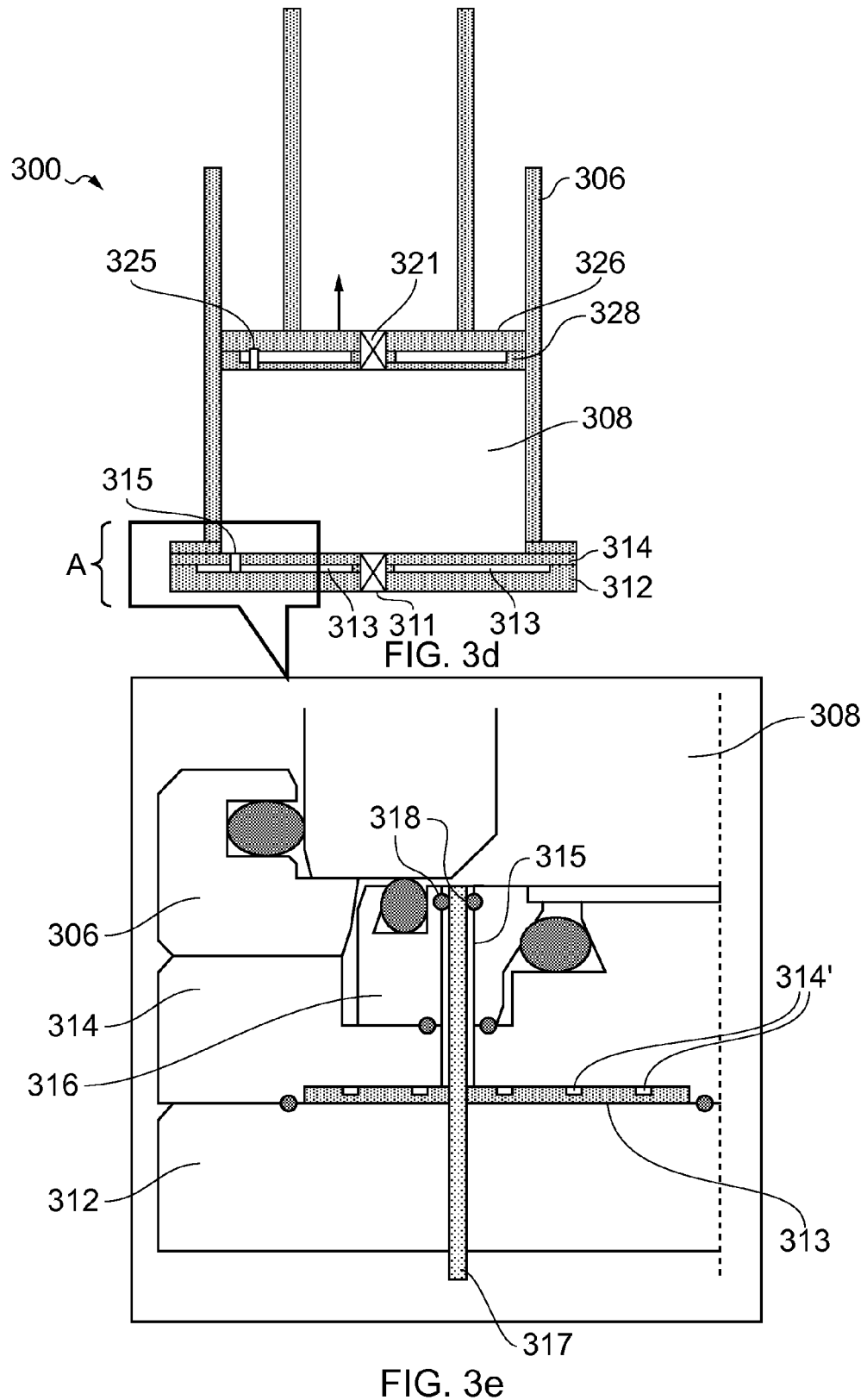
FIG. 3d is a sectional front elevation of the column of FIGS. 3a to c wherein the passages 315 and 313 are closed.
FIG. 3e is an inset of portion a of the column of FIG. 3d.

The final step in the process of securing the distributor plate 314 to the backing plate 312 is depicted in FIGS. 3d and 3e. Passage 315 is closed and then port 311 and/or 321 is opened to give atmospheric pressure within the cavity 308 and a negative pressure within the pocket 313, thus establishing a differential pressure across the distributor plate 314 (FIG. 3d) which secures distributor plate 314 to the backing plate 312.

FIG. 3e is an enlarged inset giving the detail of section A of the column 300, in which the component parts are identical to those described for FIG. 3c above. In FIG. 3e, the actuator 317 has been drawn to form a seal with gasket/o-ring 315 and effectively close base passage 315 to the influx or efflux of air.

The column may now be primed and filled with chromatographic media.

To separate the base backing plate 312 from the distributor plate 314, adapter 317 is retracted from its sealing position with gasket/o-ring 318 to open passage 315 and release the vacuum within the pocket 313. Once the vacuum has been released, the backing plate 312 and the distributor plate 314 are no longer secured together.

Figure 4A:
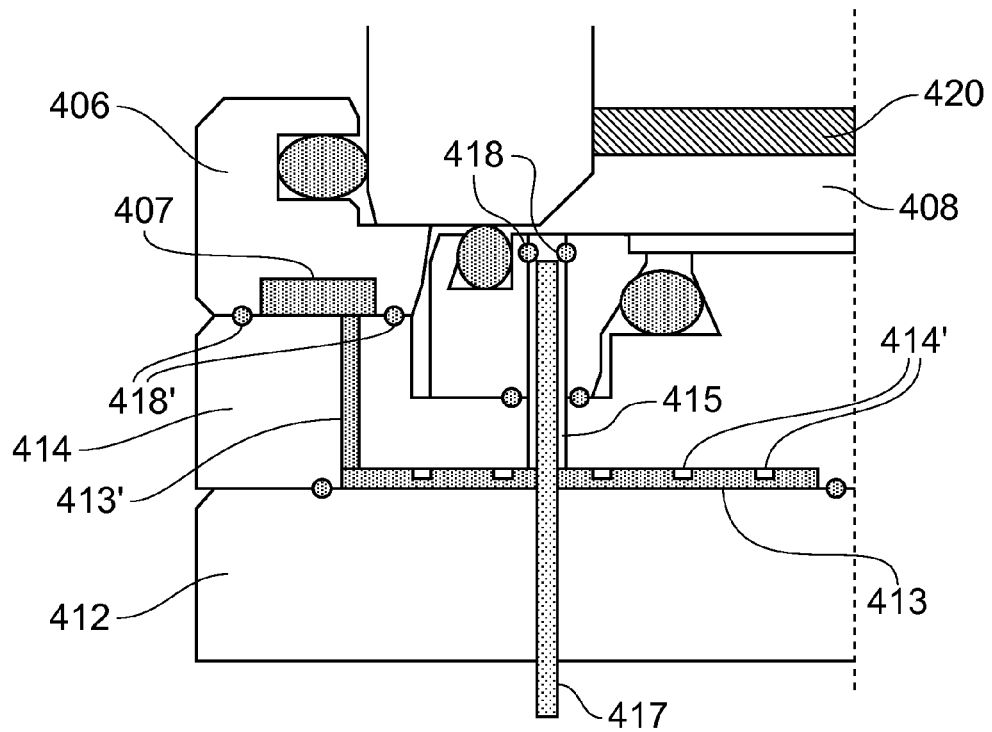
FIG. 4a is a sectional front elevation of a column before a vacuum is applied and passage 415 is in an open configuration.
Figure 4B:
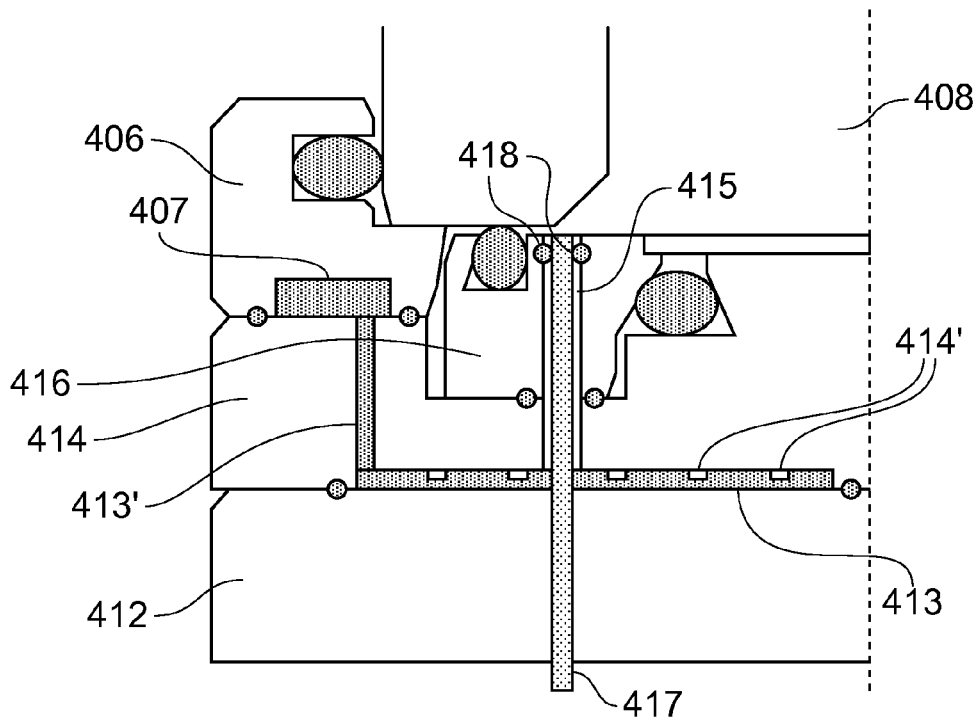
FIG. 4b is a sectional front elevation of the column of FIG. 4a after a vacuum has been applied.

FIGS. 4a and 4b are schematic sectional views of a column according to the invention which has been modified to secure the base distributor plate to the backing plate and to the column tube by means of an internally generated vacuum.

FIG. 4a shows a portion of a column, which is essentially identical to that shown in FIG. 3c described above, except that the air pocket 413 between the base backing plate 412 and the distributor 414 has been extended 413' to be in fluid communication with an air pocket or hollow 407 in the column tube 406 and that gaskets 418' provide an air-tight seal between the base of the column tube 406 and distributor plate 414. In the arrangement shown, with the adapter assembly 420 having removed air from cavity 408 (as described for FIG. 3a above), actuator 415 is not in sealing contact with gasket/o-ring 418 such that the column cavity 408 is in fluid communication with air pocket 413 and hollow 407 via air pocket 413'.

As described above, the actuator 417 will be in this open or resting position when there is no vacuum within the cavity 413. The adapter 420 and base assemblies are then drawn apart, typically by raising the adapter assembly 420 within the tube 406, to draw air from the air pocket 413, 413' and hollow 407 via open passage 415.

The last step in the process of securing the distributor plate 414 to the backing plate 412 and the column tube 406 is shown in FIG. 4b. Passage 415 is closed when adapter 417 moves to form a seal with gasket/o-ring 418. Port 311 and/or 321 is opened (see FIG. 3d) to give atmospheric pressure within the cavity 408 and a negative pressure within the pocket 413, 413' and hollow 407. This establishes a differential pressure across the distributor plate 414, which secures distributor plate 414 to the backing plate 412, and between the distributor plate 414 and the column tube 406. The distributor plate 414 is strengthened or reinforced by, for example, ribbing 414' to prevent distortion of the plate when it is subjected to a differential pressure.

To separate the distributor plate 414 from the backing plate 412 and the column tube 406, adapter 417 is moved to open passage 415 and release the vacuum within pocket 413, 413' and hollow 407.

Whilst the present invention has been described in accordance with various aspects and preferred embodiments, it is to be understood that the scope of the invention is not considered to be limited solely thereto and that it is the Applicant's intention that all variants and equivalents thereof also fall within the scope of the appended claims.

The invention claimed is:

1. A method of securing a distributor plate to a backing plate of an adaptor assembly of a chromatography column comprising:
    providing the distributor plate and the backing plate of the adaptor assembly and a base assembly;
        wherein the distributor plate and the backing plate of the adaptor assembly have an air pocket therebetween;
        wherein the base assembly and the adaptor assembly have a cavity therebetween;
        wherein the adaptor assembly is movable within the cavity of the chromatography column;

wherein the air pocket is in fluid connection with the cavity via an adapter passage in the distributor plate of the adaptor assembly; and wherein the chromatography column comprises an adapter port putting the cavity in fluid connection with an exterior of the chromatography column;

closing fluid communication through the adapter port and through the adapter passage; and moving the adaptor assembly within the cavity so that an internal vacuum is created between the distributor plate and the backing plate.

2. The method of claim 1, further comprising:
closing the adapter port;
opening the adapter passage;
moving the adapter assembly away from the base assembly to remove air from the air pocket; and
closing the passage to secure the distributor plate to the backing plate.

3. The method of claim 1, wherein the face of the distributor plate in contact with the backing plate is reinforced.

4. The method of claim 3, wherein the distributor plate is reinforced by ribbing.

5. The method of claim 1, further comprising using locating means to co-locate the backing plate and the distributor plate.

6. The method of claim 1, further comprising the step of allowing air to return to the air pocket to release the distributor plate from the backing plate.

7. The method of claim 1, further comprising the step of securing the chromatography column to the base distributor plate by generating an internal vacuum therebetween.

8. A method of securing a distributor plate to a backing plate of a base assembly of a chromatography column comprising:

providing the distributor plate and the backing plate of the base assembly and an adapter assembly;

wherein the distributor plate and the backing plate of the base assembly have an air pocket therebetween;

wherein the base assembly and the adaptor assembly have a cavity therebetween;

wherein the base assembly is movable within the cavity of the chromatography column;

wherein the air pocket is in fluid connection with the cavity via a base passage in the distributor plate of the base assembly; and wherein the chromatography column comprises a base port putting the cavity in fluid connection with an exterior of the chromatography column;

closing fluid communication through the base port and through the base passage; and moving the base assembly within the cavity so that an internal vacuum is created between the distributor plate and the backing plate.

9. The method of claim 8, further comprising:
closing the base port;
opening the base passage;
moving the base assembly away from the adapter assembly to remove air from the air pocket; and
closing the base passage to secure the distributor plate to the backing plate.

10. The method of claim 9, wherein the face of the distributor plate in contact with the backing plate is reinforced.

11. The method of claim 10, wherein the distributor plate is reinforced by ribbing.

12. The method of claim 9, further comprising using locating means to co-locate the backing plate and the distributor plate.

13. The method of claim 9, further comprising the step of allowing air to return to the air pocket to release the distributor plate from the backing plate.

14. The method of claim 9, further comprising the step of securing the chromatography column to the base distributor plate by generating an internal vacuum therebetween.

* * * * *